US012426803B2

(12) United States Patent
Johnson et al.

(10) Patent No.: US 12,426,803 B2
(45) Date of Patent: Sep. 30, 2025

(54) ENDOLUMINAL SIZING DEVICE (71) Applicant: Gyrus ACMI, Inc., Westborough, MA (US)

(72) Inventors: Timothy J. Johnson, Kent, WA (US); Brandon James Shuman, Kirkland, WA (US); David H. Dillard, Grapeview, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 232 days.

(21) Appl. No.: 17/471,058

(22) Filed: Sep. 9, 2021

(65) Prior Publication Data

US 2022/0022775 A1  Jan. 27, 2022

Related U.S. Application Data (63) Continuation of application No. 15/300,408, filed as application No. PCT/US2015/023410 on Mar. 30, 2015, now Pat. No. 11,602,286.

(Continued)

(51) Int. Cl.
*A61B 5/107* (2006.01)
*A61B 1/012* (2006.01)
(Continued)

(52) U.S. Cl.
CPC ............ *A61B 5/1076* (2013.01); *A61B 1/012* (2013.01); *A61B 1/015* (2013.01); *A61B 1/018* (2013.01);
(Continued)

(58) Field of Classification Search
CPC ............ A61B 1/00; A61B 1/012; A61B 1/018; A61B 1/267; A61B 5/1076; A61B 90/06;
(Continued)

(56) References Cited

U.S. PATENT DOCUMENTS 5,797,960 A    8/1998  Stevens et al.
6,071,233 A *  6/2000  Ishikawa .............. A61B 1/0014
                                                        600/129

(Continued)

FOREIGN PATENT DOCUMENTS

CN    1842354 A    10/2006
CN    1993083 A    7/2007
(Continued)

OTHER PUBLICATIONS

"U.S. Appl. No. 15/300,408, Advisory Action mailed Jan. 24, 2022", 4 pgs.

(Continued)

*Primary Examiner* — May A Abouelela
*Assistant Examiner* — Yasmeen S Warsi
(74) *Attorney, Agent, or Firm* — Schwegman Lundberg & Woessner, P.A.

(57) ABSTRACT

Embodiments of a sizing device that can be used to measure the size of airways lumens, such as those connected to lungs. The sizing device can have different expandable elements in order to accurately and consistently measure the particular dimensions of a lumen. In some embodiments, markings viewable by a user can be used to determine the particular size.

15 Claims, 5 Drawing Sheets

Related U.S. Application Data (60) Provisional application No. 61/973,137, filed on Mar. 31, 2014, provisional application No. 61/973,105, filed on Mar. 31, 2014, provisional application No. 61/973,110, filed on Mar. 31, 2014, provisional application No. 61/973,169, filed on Mar. 31, 2014, provisional application No. 61/973,142, filed on Mar. 31, 2014.

(51) Int. Cl.

| | | |
|---|---|---|
| *A61B 1/015* | (2006.01) | |
| *A61B 1/018* | (2006.01) | |
| *A61B 1/06* | (2006.01) | |
| *A61B 1/267* | (2006.01) | |
| *A61B 5/08* | (2006.01) | |
| *A61B 90/00* | (2016.01) | |
| *A61F 2/04* | (2013.01) | |
| *A61B 1/04* | (2006.01) | |
| *A61B 1/07* | (2006.01) | |
| *A61B 5/103* | (2006.01) | |

(52) U.S. Cl.
CPC .......... *A61B 1/0623* (2013.01); *A61B 1/0676* (2013.01); *A61B 1/0684* (2013.01); *A61B 1/267* (2013.01); *A61B 1/2676* (2013.01); *A61B 5/08* (2013.01); *A61B 5/1079* (2013.01); *A61B 90/06* (2016.02); *A61F 2/04* (2013.01); *A61B 1/04* (2013.01); *A61B 1/0661* (2013.01); *A61B 1/07* (2013.01); *A61B 5/103* (2013.01); *A61B 5/107* (2013.01); *A61B 2090/061* (2016.02); *A61F 2002/043* (2013.01); *A61F 2220/0016* (2013.01)

(58) Field of Classification Search
CPC ....... A61B 1/2676; A61B 1/32; A61B 8/4444; A61B 8/445; A61B 8/4455; A61B 1/0676; A61B 5/08; A61M 25/0105; A61M 25/0108
See application file for complete search history.

(56) References Cited

U.S. PATENT DOCUMENTS

| | | | |
|---|---|---|---|
| 7,434,578 B2 | 10/2008 | Dillard et al. | |
| 7,691,151 B2 | 4/2010 | Kutsko et al. | |
| 7,909,803 B2 | 3/2011 | Tanaka | |
| 7,942,931 B2 | 5/2011 | Gonzalez et al. | |
| 8,043,301 B2 | 10/2011 | Adams et al. | |
| 8,475,389 B2 | 7/2013 | Tanaka et al. | |
| 8,518,053 B2 | 8/2013 | Tanaka et al. | |
| 8,905,937 B2* | 12/2014 | Ellingwood | A61B 5/0538 |
| | | | 600/481 |
| 9,345,416 B2 | 5/2016 | Macadam et al. | |
| 11,602,286 B2 | 3/2023 | Shuman | |
| 2001/0039388 A1* | 11/2001 | Korotko | A61B 5/1076 |
| | | | 600/587 |
| 2003/0176886 A1 | 9/2003 | Wholey et al. | |
| 2003/0216769 A1 | 11/2003 | Dillard et al. | |
| 2004/0060563 A1 | 4/2004 | Rapacki et al. | |
| 2004/0143282 A1 | 7/2004 | Dillard et al. | |
| 2005/0010138 A1* | 1/2005 | Mangiardi | A61B 5/1076 |
| | | | 600/587 |
| 2006/0015137 A1 | 1/2006 | Wasdyke et al. | |
| 2006/0064039 A1* | 3/2006 | Griego | A61B 5/1076 |
| | | | 600/587 |
| 2007/0106296 A1 | 5/2007 | Laufer et al. | |
| 2007/0123851 A1 | 5/2007 | Alejandro et al. | |
| 2008/0072914 A1 | 3/2008 | Hendricksen et al. | |
| 2008/0275496 A1* | 11/2008 | Fleming | A61F 2/01 |
| | | | 606/200 |
| 2009/0143705 A1 | 6/2009 | Danek et al. | |
| 2009/0157043 A1 | 6/2009 | Leonard et al. | |
| 2009/0287050 A1 | 11/2009 | Barthel | |
| 2010/0036241 A1* | 2/2010 | Mayse | A61B 1/018 |
| | | | 600/435 |
| 2010/0160832 A1 | 6/2010 | Braido | |
| 2010/0199999 A1* | 8/2010 | Vazales | A61B 90/70 |
| | | | 128/207.14 |
| 2011/0023885 A1 | 2/2011 | Vazales et al. | |
| 2011/0098602 A1 | 4/2011 | Campbell et al. | |
| 2012/0053485 A1 | 3/2012 | Bloom | |
| 2012/0179086 A1 | 7/2012 | Shank et al. | |
| 2012/0184985 A1 | 7/2012 | Ravenscroft et al. | |
| 2012/0209308 A1 | 8/2012 | Kutsko et al. | |
| 2013/0253492 A1 | 9/2013 | Danek et al. | |
| 2013/0345519 A1* | 12/2013 | Piskun | A61M 29/02 |
| | | | 600/204 |
| 2017/0181665 A1 | 6/2017 | Johnson | |

FOREIGN PATENT DOCUMENTS

| | | |
|---|---|---|
| CN | 101460113 A | 6/2009 |
| CN | 102470028 A | 5/2012 |
| CN | 102762156 A | 10/2012 |
| CN | 106413588 A | 2/2017 |
| CN | 106413588 B | 4/2020 |
| CN | 111513662 A | 8/2020 |
| EP | 2475328 B1 | 8/2014 |
| EP | 3125782 A1 | 2/2017 |
| EP | 3125782 B1 | 9/2021 |
| JP | 2009532098 A | 9/2009 |
| JP | 2013226429 A | 11/2013 |
| JP | 2017510360 A | 4/2017 |
| JP | 2020022805 A | 2/2020 |
| JP | 6935197 B2 | 8/2021 |
| JP | 6995817 B2 | 12/2021 |
| WO | WO-2004006767 A2 | 1/2004 |
| WO | WO-2007134587 A2 | 11/2007 |
| WO | WO-2013109398 A1 | 7/2013 |
| WO | WO-2015153500 A1 | 10/2015 |
| WO | WO-2015153507 A1 | 10/2015 |

OTHER PUBLICATIONS

"U.S. Appl. No. 15/300,408, Advisory Action mailed Feb. 9, 2022", 3 pgs.
"U.S. Appl. No. 15/300,408, Advisory Action mailed Mar. 3, 2020", 4 pgs.
"U.S. Appl. No. 15/300,408, Advisory Action mailed Jun. 4, 2021", 3 pgs.
"U.S. Appl. No. 15/300,408, Advisory Action mailed Jun. 19, 2019", 3 pgs.
"U.S. Appl. No. 15/300,408, Applicant's Summary of Examiner Interview filed Jun. 16, 2021", 11 pgs.
"U.S. Appl. No. 15/300,408, Examiner Interview Summary mailed Jun. 15, 2021", 2 pgs.
"U.S. Appl. No. 15/300,408, Examiner Interview Summary mailed Jun. 18, 2021", 2 pgs.
"U.S. Appl. No. 15/300,408, Final Office Action mailed Mar. 8, 2019", 11 pgs.
"U.S. Appl. No. 15/300,408, Final Office Action mailed Mar. 30, 2021", 13 pgs.
"U.S. Appl. No. 15/300,408, Final Office Action mailed Sep. 1, 2022", 12 pgs.
"U.S. Appl. No. 15/300,408, Final Office Action mailed Nov. 4, 2021", 15 pgs.
"U.S. Appl. No. 15/300,408, Final Office Action mailed Dec. 23, 2019", 13 pgs.
"U.S. Appl. No. 15/300,408, Non Final Office Action mailed Apr. 18, 2022", 14 pgs.
"U.S. Appl. No. 15/300,408, Non Final Office Action mailed May 19, 2020", 14 pgs.
"U.S. Appl. No. 15/300,408, Non Final Office Action mailed Jul. 30, 2021", 16 pgs.
"U.S. Appl. No. 15/300,408, Non Final Office Action mailed Sep. 25, 2019", 11 pgs.

(56) References Cited

OTHER PUBLICATIONS

"U.S. Appl. No. 15/300,408, Non Final Office Action mailed Oct. 2, 2018", 14 pgs.
"U.S. Appl. No. 15/300,408, Notice of Allowance mailed Nov. 9, 2022", 10 pgs.
"U.S. Appl. No. 15/300,408, Response filed Jan. 4, 2022 to Final Office Action mailed Nov. 4, 2021", 8 pgs.
"U.S. Appl. No. 15/300,408, Response filed Jan. 25, 2022 to Advisory Action mailed Jan. 24, 2022", 12 pgs.
"U.S. Appl. No. 15/300,408, Response filed Jan. 27, 2021 to Non Final Office Action mailed May 19, 2020", 12 pgs.
"U.S. Appl. No. 15/300,408, Response filed Feb. 24, 2020 to Final Office Action mailed Dec. 23, 2019", 6 pgs.
"U.S. Appl. No. 15/300,408, Response filed Mar. 23, 2020 to Advisory Action mailed Mar. 3, 2020", 5 pgs.
"U.S. Appl. No. 15/300,408, Response filed May 28, 2021 to Final Office Action mailed Mar. 30, 2021", 11 pgs.
"U.S. Appl. No. 15/300,408, Response filed Jun. 4, 2019 to Final Office Action mailed Mar. 8, 2019", 5 pgs.
"U.S. Appl. No. 15/300,408, Response filed Jun. 16, 2021 to Advisory Action mailed Jun. 4, 2021", 11 pgs.
"U.S. Appl. No. 15/300,408, Response filed Jul. 2, 2019 to Advisory Action mailed Jun. 19, 2019", 5 pgs.
"U.S. Appl. No. 15/300,408, Response filed Jul. 12, 2022 to Non Final Office Action mailed Apr. 18, 2022", 8 pgs.
"U.S. Appl. No. 15/300,408, Response filed Sep. 27, 2021 to Non Final Office Action mailed Jul. 30, 2021", 9 pgs.
"U.S. Appl. No. 15/300,408, Response filed Oct. 24, 2022 to Final Office Action mailed Sep. 1, 2022", 9 pgs.
"U.S. Appl. No. 15/300,408, Response filed Dec. 10, 2019 to Non Final Office Action mailed Sep. 25, 2019", 6 pgs.
"U.S. Appl. No. 15/300,408, Response filed Dec. 27, 2018 to Non Final Office Action mailed Oct. 2, 2018", 5 pgs.
"Chinese Application Serial No. 202010372692.8, Office Action mailed Mar. 1, 2023", w/ English Translation, 18 pgs.
"European Application Serial No. 15773018.5, Extended European Search Report mailed Mar. 21, 2018", 13 pgs.
"European Application Serial No. 15773018.5, Intention to Grant mailed Mar. 22, 2021", 102 pgs.
"European Application Serial No. 15773018.5, Intention to Grant mailed Nov. 4, 2020", 100 pgs.
"European Application Serial No. 15773018.5, Response filed Mar. 4, 2021 to Intention to Grant mailed Nov. 4, 2020", 5 pgs.
"European Application Serial No. 15773018.5, Response filed Oct. 2, 2018 to Extended European Search Report mailed Mar. 21, 2018", 67 pgs.
"European Application Serial No. 15773018.5, Supplementary Partial European Search Report mailed Dec. 11, 2017", 13 pgs.
"European Application Serial No. 15773018.5, Supplementary Partial European Search Report mailed Dec. 14, 2017", 14 pgs.
"International Application Serial No. PCT/US2015/023410, International Preliminary Report on Patentability mailed Oct. 13, 2016", 8 pgs.
"International Application Serial No. PCT/US2015/023410, International Search Report mailed Jul. 7, 2015", 2 pgs.
"International Application Serial No. PCT/US2015/023410, Written Opinion mailed Jul. 7, 2015", 6 pgs.
"International Application Serial No. PCT/US2015/023421, International Preliminary Report on Patentability mailed Oct. 13, 2016", 8 pgs.
"International Application Serial No. PCT/US2015/023421, International Search Report mailed Jul. 7, 2015", 2 pgs.
"International Application Serial No. PCT/US2015/023421, Written Opinion mailed Jul. 7, 2015", 6 pgs.
"Japanese Application Serial No. 2016-559835, Decision of Refusal mailed Jul. 1, 2019", w/ English translation, 9 pgs.
"Japanese Application Serial No. 2016-559835, Notification of Reasons for Refusal mailed Mar. 8, 2021", w/ English translation, 4 pgs.
"Japanese Application Serial No. 2016-559835, Notification of Reasons for Refusal mailed Sep. 7, 2020", w/ English translation, 12 pgs.
"Japanese Application Serial No. 2016-559835, Notification of Reasons for Refusal mailed Nov. 12, 2018", w/ English translation, 8 pgs.
"Japanese Application Serial No. 2016-559835, Response filed Feb. 8, 2019 to Notification of Reasons for Refusal mailed Nov. 12, 2018", w/ English claims, 14 pgs.
"Japanese Application Serial No. 2016-559835, Response filed Jun. 2, 2021 to Notification of Reasons for Refusal mailed Mar. 8, 2021", with English claims, 8 pgs.
"Japanese Application Serial No. 2016-559835, Response filed Oct. 25, 2019 to Decision of Refusal mailed Jul. 1, 2019", with English claims, 20 pgs.
"Japanese Application Serial No. 2016-559835, Response filed Nov. 6, 2020 to Notification of Reasons for Refusal mailed Sep. 7, 2020", with English claims, 12 pgs.
"Japanese Application Serial No. 2019-194533, Decision of Refusal mailed Jun. 14, 2021", w/ English translation, 5 pgs.
"Japanese Application Serial No. 2019-194533, Notification of Reasons for Refusal mailed Feb. 22, 2021", w/ English translation, 6 pgs.
"Japanese Application Serial No. 2019-194533, Response filed May 20, 2021 to Notification of Reasons for Refusal mailed Feb. 22, 2021", w/ English claims, 6 pgs.
"Japanese Application Serial No. 2019-194533, Response filed Oct. 14, 2021 to Decision of Refusal mailed Jun. 14, 2021", w/ English claims, 2 pgs.
"Chinese Application Serial No. 202010372692.8, Response filed Jul. 4, 2023 to Office Action mailed Mar. 1, 2023", w/ english claims, 10 pgs.
"Chinese Application Serial No. 202010372692.8, Decision of Rejection mailed Feb. 1, 2024", with machine translation, 15 pgs.
"Chinese Application Serial No. 202010372692.8, Response filed Dec. 6, 2023 to Office Action mailed Sep. 27, 2023", w/ english claims, 7 pgs.
"Chinese Application Serial No. 202010372692.8, Office Action mailed Sep. 27, 2023", W/O English Translation, 6 pgs.
"Chinese Application Serial No. 202010372692.8, Response filed Apr. 25, 2024 to Decision of Rejection mailed Feb. 1, 2024", w/ english claims, 10 pgs.

* cited by examiner

ENDOLUMINAL SIZING DEVICE

INCORPORATION BY REFERENCE TO ANY PRIORITY APPLICATIONS

This application is a Continuation Application of U.S. application Ser. No. 15/300,408, filed Sep. 29, 2016, which claims the benefit of U.S. Provisional Application Nos. 61/973,105, filed Mar. 31, 2014, titled "SIMULATED VALVE DEVICE FOR AIRWAY", 61/973,110, filed Mar. 31, 2014, titled "ENDOBRONCHIAL BRUSH DEVICE TO ESTIMATE SIZE OF AIRWAYS", 61/973,137, filed Mar. 31, 2014, titled "LIGHT-BASED ENDOLUMINAL SIZING DEVICE", 61/973,169, filed Mar. 31, 2014, titled "ENDOLUMINAL SIZING DEVICE", and 61/973,142, filed Mar. 31, 2014, titled "ANCHORING MECHANISMS AND SYSTEMS FOR ENDOLUMINAL DEVICES", the entirety of each of which is hereby incorporated by reference.

BACKGROUND

This disclosure relates generally to embodiments of devices that measure the size of airways to lungs.

SUMMARY

Disclosed herein are embodiments of an endoluminal sizing device comprising a shaft movable along an axis of a lumen, and a size determining portion attached to the shaft, the size determining portion comprising a plurality of expandable members, wherein the expandable members are configured to expand to an endoluminal wall of the lumen, wherein the size determining portion comprises an indication of a size of the lumen.

In some embodiments, the device can further comprise a sheath that at least partially surrounds the size determining portion, wherein the sheath prevents the expandable members from expanding until removal of the sheath. In some embodiments, the sheath can be configured to contract the expandable members upon the size determining portion translating into the sheath.

In some embodiments, the size determining portion can further comprise a hub connected to a distal end of the shaft, and the expandable members comprise a plurality of struts extending radially outward from the hub, and a plurality of whiskers attached to a surface of the struts facing the endoluminal wall, wherein the plurality of whiskers extend away from the surface of the struts facing the endoluminal wall, wherein the plurality of whiskers fold down flush with the surface of the struts when the surface of the struts contact the endoluminal wall, and wherein a number of the plurality of whiskers unfurled away from the surface of the struts indicate a sizing of the lumen.

In some embodiments, each strut can have a plurality of whiskers. In some embodiments, the whiskers can have a thickness less than the struts. In some embodiments, the plurality of struts can be configured to fold down against the surface of the hub.

In some embodiments, the device can further comprise a blocking mechanism located at a distal end of the size determining portion, the expandable members comprising a plurality of wires extending substantially perpendicular from the blocking mechanism wherein compressing the plurality of wires against the blocking mechanism radially expands the plurality of wires to contact the endoluminal wall and wherein a change in a longitudinal distance of the plurality of wires before and after the size determining portion contacts the endoluminal wall indicates the sizing of the lumen.

In some embodiments, compressing can occur by a force acting on the plurality of wires. In some embodiments, compressing can occur by a force acting on the blocking mechanism. In some embodiments, the blocking mechanism can be attached to an inner surface of a catheter, and the plurality of wires is configured to expand through apertures in the catheter.

In some embodiments, the device can further comprise a measuring disc having slots configured to receive free ends of the expandable members having a general basket shape, the measuring disc further having markings to indicate expansion and contraction of a size determining portion, and a centering portion connecting and aligning the measuring disc and the size determining portion wherein the location of the free ends of the expandable members on the measuring disc indicates a size of the lumen.

In some embodiments, the expandable members can comprise wires formed into an expandable basket. In some embodiments, insertion of the device into the lumen does not irritate or damage the lumen.

Also disclosed herein are embodiments of a method of using an endoluminal sizing device for sizing a body lumen comprising deploying the endoluminal sizing device inside the body lumen, the endoluminal sizing device comprising a shaft movable along an axis of a lumen, and a size determining portion attached to the shaft, the size determining portion comprising a plurality of expandable members, wherein the expandable members are configured to expand to an endoluminal wall of the lumen, and determining the endoluminal size from a visual change in the size determining portion.

In some embodiments, the size determining portion can further comprise a hub connected to a distal end of the shaft, and the expandable members comprise a plurality of struts extending radially outward from the hub, and a plurality of whiskers attached to a surface of the struts facing the endoluminal wall wherein the plurality of whiskers extend away from the surface of the struts facing the endoluminal wall wherein the plurality of whiskers fold down flush with the surface of the struts when the surface of the struts contact the endoluminal wall; and wherein determining the endoluminal size comprises determining a number of the plurality of whiskers unfurled away from the surface of the struts.

In some embodiments, the endoluminal sizing device can further comprise a blocking mechanism located at a distal end of the size determining portion, the expandable members comprising a plurality of wires extending substantially perpendicular from the blocking mechanism, wherein compressing the plurality of wires against the blocking mechanism radially expands the plurality of wires to contact the endoluminal wall, and wherein a change in a longitudinal distance of the plurality of wires before and after the size determining portion contacts the endoluminal wall indicates the sizing of the lumen.

In some embodiments, compressing can occur by a force acting on the plurality of wires. In some embodiments, compressing can occur by a force acting on the blocking mechanism.

In some embodiments, the endoluminal sizing device can farther comprise a measuring disc having slots configured to receive free ends of the expandable members having a general basket shape, the measuring disc further having markings to indicate expansion and contraction of a size determining portion, and a centering portion connecting and aligning the measuring disc and the size determining portion, wherein determining the endoluminal size comprises reading the location of the free ends of the expandable members on the measuring disc.

DETAILED DESCRIPTION

Disclosed herein are embodiments of devices that can be used for measuring or approximating the size of airways, specifically the dimensions of the lumen of the airways. For example, embodiments of the device can be used to measure dimensions of the airways leading into a person's, or animal's, lungs. However, the disclosed devices can be used to measure other lumens as well, and the particular lumen being measuring is not limiting. Further, the measured dimensions can be, for example, volume, radius, circumference or diameter, though the particular dimensions are not limiting.

In some embodiments, the size variations that can be determined by embodiments of the device can depend on the size of the lumen being measured and the device being measured for. As way of example, for segmented airways, the diameters of the airways can be on the order of about 3 mm to about 12 mm, and embodiments of the disclosed device can measure to approximately + or −0.05, 0.10, 0.20, 0.25, 0.30, 0.40, or 0.50 mm. In some embodiments. the measurements are a resolution between to device sizes, e.g., a 7 mm or 6 mm device. Embodiments of the disclosed devices can accurately indicate when an airway is above or below the size of a particular device for proper fitting. The particular dimensions being measured are not limiting.

Typically, airways should be measured before other devices, such as intra-bronchial valves, tracheal tubes, or other devices are inserted into lungs. This measurement should be done prior to the insertion of the intended device in order to reduce the likelihood that an inappropriately-sized device is used in an airway, thus inhibiting or preventing damage to the airway based on too large, or too small of a device. For example, too large of a device for the diameter of an airway can lead to permanent rupturing or deformation of the airway.

Advantageously, embodiments of the disclosed devices can determine very small differences in the size of airways, which can be difficult, providing a user with accurate sizing data. Certain embodiments can be configured to approximate a size of a target airway within a predetermined size range (e.g., a predetermined diameter range). The sizing data can allow for insertion of further equipment into the airways which may otherwise damage or irritate the airways if the airways were not properly sized. In some embodiments, the disclosed sizing devices can advantageously center themselves in the lumen airway, exert relatively low radial force against the airway wall, and/or provide a method to mechanically measure or gauge the size of the airway.

Certain previous catheters use tangs to indicate when an airway is too big for a device. With flexible tangs of different heights away from the center of a catheter, the operator can determine if the airway is in a certain range of diameters Other devices use an expanding triangle configuration. These devices use a catheter that has a pull wire, which, when pulled back, expands two opposing members. When the members touch the wall of the airway, the user can read the diameter off of the handle.

However, the airway walls can have varying degrees of compliance and mechanical sizing tools can displace the walls leading to measurement error, which can lead to the use of an improperly sized medical device, a problem that is common in the prior art. Further, tools that do not self-center can erroneously measure a cross-sectional chord rather than an actual diameter of the airway lumen. Moreover, some airways are not cylindrical, but can be tapered along the length or non-circular in cross section, leading to incorrect measurements. Thus, there are significant disadvantages to the airway lumen measuring devices that are currently being used.

Sizing Device

Disclosed herein are embodiments of sizing, or measuring, devices for measuring airways and airway lumens leading to lungs. In some embodiments, the sizing device can measure or approximate small to large variations in the size of airways, for example those leading to lungs. In some embodiments, these devices can be inserted directly into the airways in order to internally measure the size of the airways with little or no deforming, irritating, or damaging of the airways themselves. Embodiments of the sizing devices can center themselves within the lumen, providing a more accurate reading. In some embodiments, an endoscope, or other visual means, can be used to view the measurement device when inserted into the lung airways to determine the inner diameter of the lung airways. In some embodiments, the size of the airways can be determined after removal and review of the sizing device.

In some embodiments. the below discussed sizing devices can be formed of a biocompatible material, such as nitinol, titanium, or steel. However, other materials, such as polymers, plastics, metals, and ceramics, can be used as well and the particular material is not limiting.

While the below disclosure discusses mainly manual methods for adjusting the measurement device, electronic, automated. or other methods of operating the measurement devices can be used as well and the methodology for insertion and expansion of the measurement device is not limiting.

Whisker Sizing Device

FIGS. 1A-D show an embodiment of an endoluminal sizing device 100 composed generally of a shaft 102 and a size determining portion 104.

In some embodiments, the shaft 102 and the size determining portion 104 can be integrally formed. In some embodiments, they may be separately formed and attached to one another through, for example, mechanical, adhesive. or chemical means. The attachment of the shaft 102 and size determining portion 104 is not limiting. In some embodiments, the size determining portion 104 may be removable from the shaft 102.

The size determining portion 104 can be configured to deploy, as further described in detail below, inside the lumen of an airway upon insertion of the device 100. In some embodiments, the size determining portion 104 may not deploy until it reaches a desired position in the airway lumen. For example, in some embodiments a sheath can be used which can at least partially, or fully, house the size determining portion 104 and/or the shaft 102. The sheath can prevent expansion of the size determining portion 104 until it is properly position. In some embodiments, a shaft 102 housed in the sheath can be pushed away from the sheath to allow insertion-then-expansion of the size determining portion 104 inside the lumen. In some embodiments, a sheath is withdrawn from the shaft 102 to deploy the size determining portion 104. However, other means for prevention of expansion of the size determining portion can be used as well, such as a catheter, working channel of a bronchoscope or endoscope, or other sheath-like device, and the particular means is not limiting.

In some embodiments, the shaft 102 can be formed as a generally cylindrical/rod-like shape having a distal end 122 and proximal end 124. However, the shaft 102 can have other shapes and dimensions as well, and the shape of the shaft 102 is not limiting. If other shapes are used, such as squares or triangles, the edges of the shaft 102 can be rounded in order to prevent any irritation of the airway. In some embodiments, the shaft 102 can be relatively rigid. In some embodiments, the shaft 102 can be generally flexible. The rigidity of the shaft is not limiting. 'The shaft 102 can be used to move the size determining portion 104 into, through, and back out of the airways leading to the lungs. In some embodiments, the shaft 102 can be made of generally biocompatible material, though the type of material is not limiting.

Figure 1A:
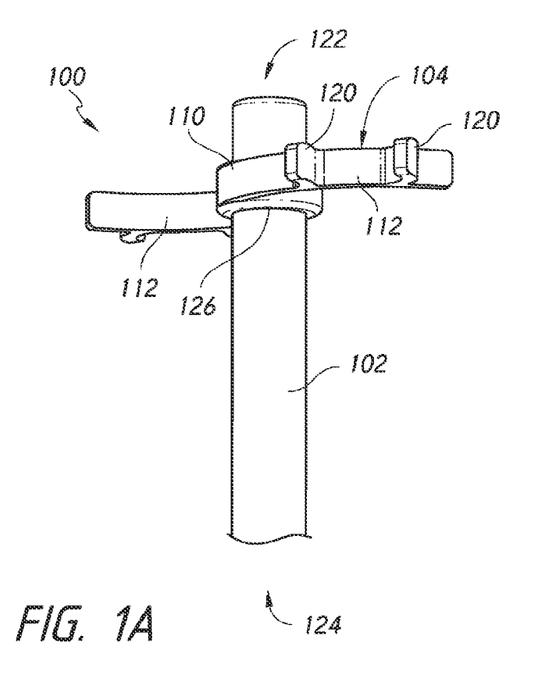
FIGS. 1A-D illustrate viewpoints of an embodiment of an airway measuring device having expandable struts.

As mentioned, the size determining portion 104 can be attached to the shaft 102 in order to move the size determining portion 104 through the airway lumens. For example, the size determining portion 104 can be attached near the distal end 122 of the shaft 102 as shown in FIG. 1A. In some embodiments, the size determining portion 104 can be located generally centered on the shaft 102. Further, as shown in FIG. 1A, the size determining portion 104 can include an aperture 126 configured to fit around the shaft 102. The aperture 126 can include a connection means to attach the size determining portion 104 to the shaft 102.

In some embodiments, the size determining portion 104 can comprise a hub 110, which may include the aperture 126, and one or more struts 112. In some embodiments, the hub 110 may have a shape generally similar to the shaft 102. For example, as shown in FIGS. 1A-D, the hub 110 can be generally circular/cylindrical, though the particular shape of the hub 100 is not limiting. In some embodiments, the hub 110 may be thin and thus cover only a small portion of the shaft 102, or may generally extend a portion of the length of the shaft 102.

In some embodiments, the hub 110 may have 1, 2, 3, 4, 5, or 6 struts 112 extending from its outer circumference, and the number of struts is not limiting. The struts 112 may be flexibly linked to the hub 110, thus allowing them to bend and wrap around the hub 110. In some embodiments, the struts 112 can be located circumferentially adjacent to one another. In some embodiments. struts 112 may not be located circumferentially adjacent, and can thus be located spaced apart along the length of the hub 110. In some embodiments, the struts 112 can have a thickness greater than die hub 110. In some embodiments, the struts 112 can have a thickness less than the hub 110. In some embodiments, the struts 112 can have a thickness the same as the hub 110.

The plurality of struts 112 can be of different lengths and sizes, and their particular dimensions are not limiting. For example, struts 112 may have generally the same size in some embodiments. In some embodiments, the struts 112 may have generally different sizes. Once deployed, the struts 112 can expand to contact the lumen wall without substantially displacing any portion of the lumen wall, and thus without irritating or damaging the airways.

As mentioned, in some embodiments, the struts 112 can be configured to expand outward from the hub 110 towards the inner surface of the lumen of an airway. In some embodiments, the struts 112 can expand radially outward from the hub 110. In some embodiments, the struts 112 can expand radially outward from the hub 110 in a rotational fashion. In some embodiments. the struts 112 can expand radially outward from the hub 110 in a linear fashion.

In some embodiments, the plurality of struts 112 can be generally spiral-shaped arms. The spiral-shaped arms can form a helix form, or can generally form the shape of a helix. The helix form of the plurality of struts 112 can be used to facilitate a seamless retraction of the spiral arms into a sheath if a sheath is being used. For example, the helix form can facilitate radial compressive force on the spiral arms as the arms are pulled into the sheath and/or as the sheath is extended over the arms. Thus, significant effort does not have to be used and there is less likelihood of breakage of the plurality of struts 112. The helix form can also allow easier manufacturing of the measuring device.

Figure 1B:
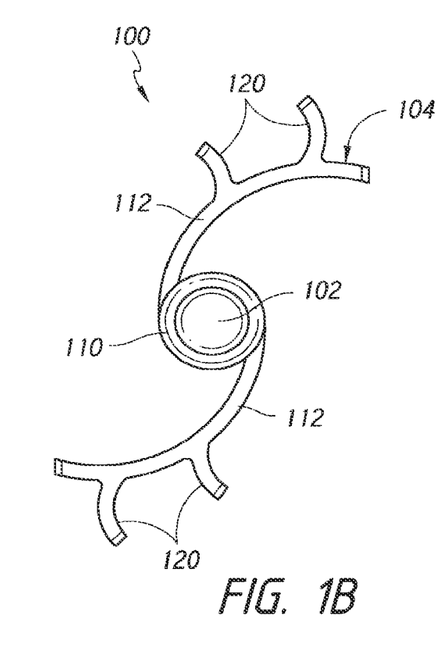
Figure 1C:
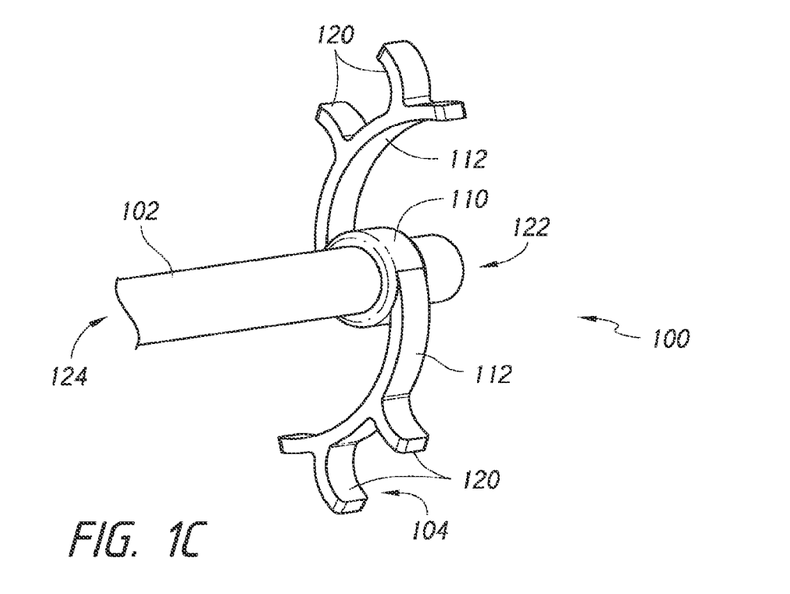

Additionally, each of the struts 112 can further include at least one small protrusion 120, such as those shown in FIGS. 1A-C. In some embodiments, the struts 112 can have a plurality of small protrusions 120. In some embodiments, the struts 112 can all have the same amount of protrusions 120. In some embodiments, the struts 112 can all have different amounts of protrusions 120. In some embodiments, the small protrusions 120 can be whiskers, or thin filament whiskers, attached to a surface of the struts 112 facing an endoluminal wall. In some embodiments, the small protrusions 120 are formed by cutting and folding away portions of the struts 112. In some embodiments, the whiskers can extend away from the surface of the strut 112 facing an endoluminal wall. In some embodiments, each protrusion 120 can have the same length. In some embodiments, protrusion 120 can have a different length.

In some embodiments, the protrusions 120 can be formed from the same material as the strut 112. For example, the protrusions 120 can be a single ribbon, strip, slice, or portion of the material of the strut 112, which would give the protrusions 120 flexibility, and may reduce any need to additionally connect the protrusions 120 to the struts 112. The protrusion 120 may be pulled back from the strut 112 to any desired position for measurement of a lumen.

Figure 1D:
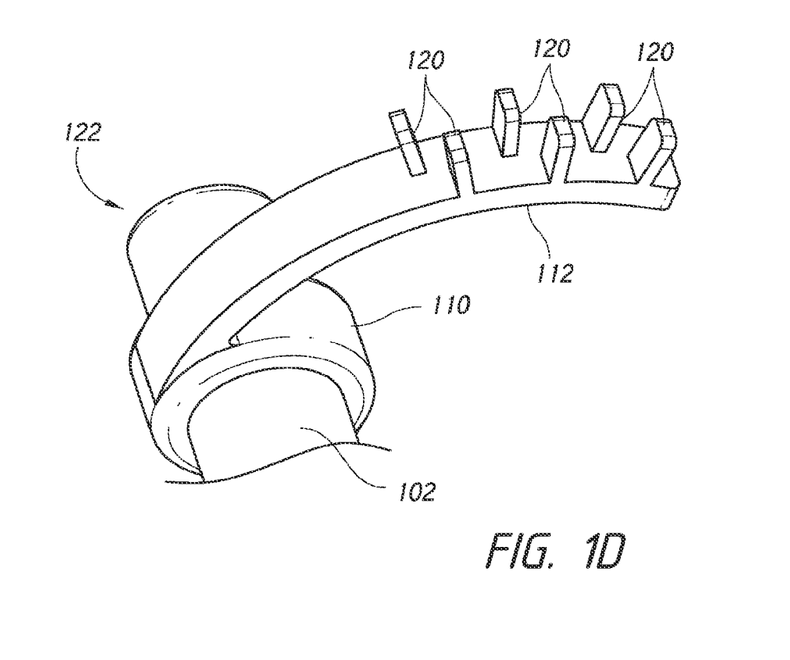

In some embodiments, the thickness of the small protrusions 120 can be smaller in comparison to the thickness of the spiral arms as shown in FIG. 1D. For example, the thickness of the struts 112 can be about 0.015 inches to about 0.020 inches, while the thickness of the small protrusions 120 can be about 0.002 inches to about 0.003 inches, though the particular dimensions are not limiting. The smaller thickness of the small protrusions 120 can allow the protrusions 120 to be more flexible than the struts 112. However, in some embodiments the struts 112 and small protrusions 120 can have generally the same thickness, as shown in FIG. 1 A-C.

In some embodiments, when the struts 112 are inside the sheath, the small protrusions 120 can fold down substantially flush with the struts 112. Once the struts 112 are outside the sheath, the struts 112 can be extended radially outward from lumen axis, and the small protrusions 120 can unfurl to contact the lumen wall without damaging or irritating the lumen wall. The extension of the struts 112 and small protrusions 120 can occur automatically when the sheath is removed and does not require further input from the user.

When located in a large lumen, only the small protrusions 120 far out on the ends of the struts 112 will fold down due to contact with the lumen wall. However, as the lumen diameter decreases, more small protrusions 120 can fold down, indicating to a user that the lumen is smaller. In some embodiments, the small protrusions 120 fold down flush with the struts 112 to indicate the lumen size. In some embodiments, the small protrusions 120 are shaped so that as they fold down, they protrude into the inner radius of the struts 112 to indicate when the strut 112 is against the wall. In some embodiments, additional markings can be used to indicate the dimensions of the lumen. For example, one or more of the small protrusions 120 or struts 112 can have a color generally corresponding to a radius or diameter of the lumen at the point of contact with the colored portion. In some embodiments, certain protrusions 120 have a first color and certain other protrusions 120 have another color to indicate varying radial positions between the respective protrusions. In some embodiments, the outward radial force imposed by the small protrusions 120 and/or struts 112 is such that the lumen wall is not substantially expanded/ displaced radially outward. Advantageously, this can inhibit or prevent damage or irritation of the airways upon use of the embodiments of a sizing device 100.

In some embodiments, the ends of small protrusions 120 can point in the same direction as the struts 112, such as in a counterclockwise direction as shown in FIGS. 1A-C. In some embodiments, the ends of small protrusions 120 can point in the opposite direction as the struts 112, such as in a clockwise direction.

In some embodiments, the small protrusions 120, or in fact any part of the device 100, can be made from nitinol, though other biocompatible metals and/or polymers can be used as well. The material forming the small protrusions 120 is not limiting. In some embodiments, the small protrusions 120 can be laser cut, though the method of forming is not limiting.

Upon insertion of the sizing device 100, a user may use medical imaging devices, such as a camera of an endoscope, to view the number, the location, and the form of expanded small protrusions 120 having different sizes. The number, the location, and the form of expanded small protrusions 120 having different sizes can indicate the sizing of the lumen. For example, a user could tell which of the small protrusions 120 was expanded, which would let a user know the particular size of the lumen. A user may know this based on markings on the device 100, or may have prior knowledge of the sizing. Further, the device 100 may be removed and a user could determine the particular size of the lumen by reviewing the device 100 after removal.

Blocking Mechanism Sizing Device

Figure 2A:
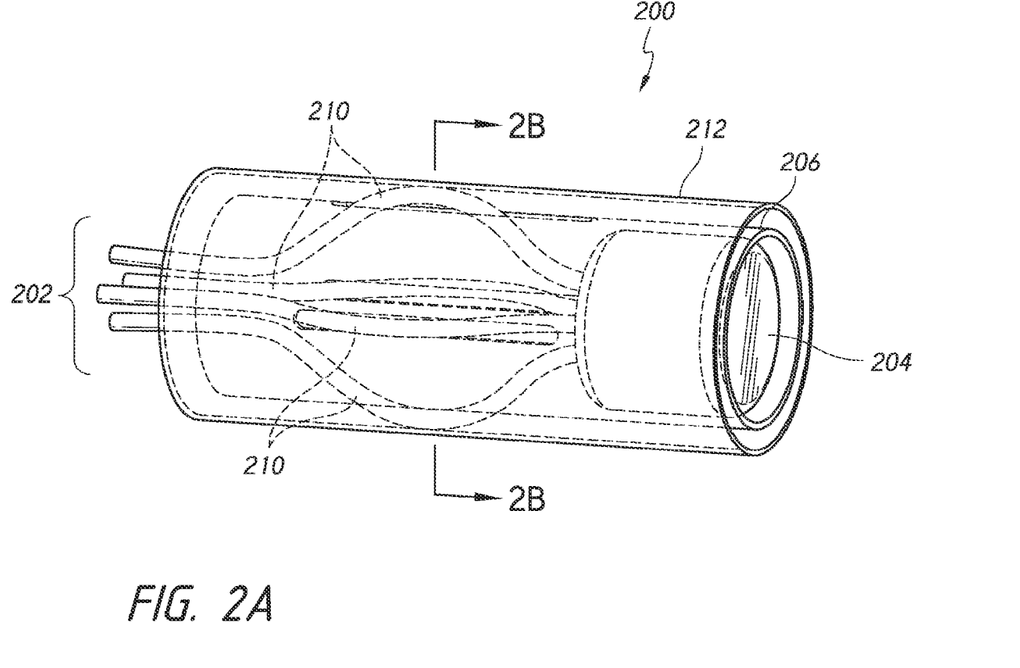
FIGS. 2A-B illustrate viewpoints of an embodiment of a blocking airway measuring device.
Figure 2B:
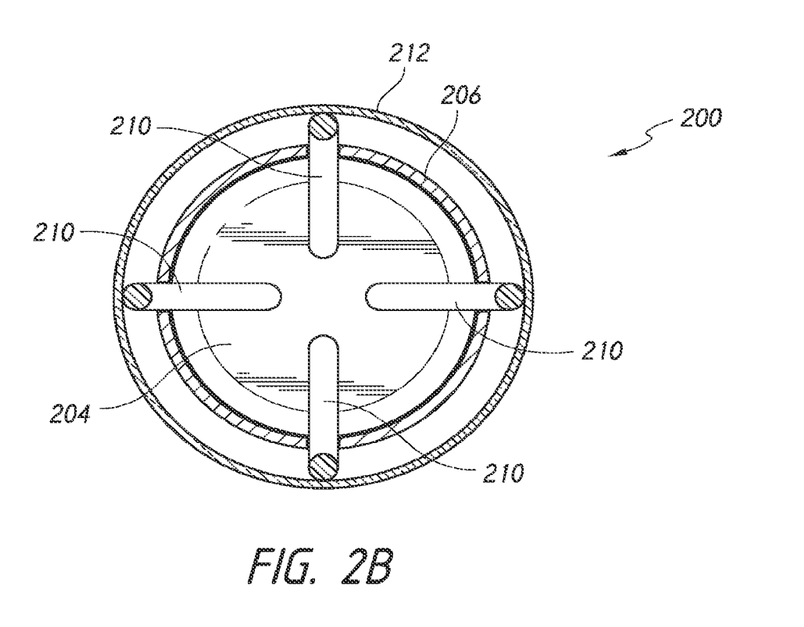

FIGS. 2A-B show an embodiment of a sizing device 200 that can include size determining portion 202 and a blocking mechanism 204.

In some embodiments, the size determining/estimating portion 202 can be a plurality of wires 210, such as a plurality of generally longitudinally extending wires as shown in FIG. 2A. The wires 210 can extend generally in the same direction as the axis of a lumen to be measured 212. In some embodiments, the wires 210 can be generally straight upon insertion into the lumen 212. In some embodiments, the wires 210 can have a bend, such as shown in FIG. 2A, which can allow for the wires 210 to further bend in a predetermined direction. In some embodiments, the wires 210 may be shapeset with a slight bump-outward. The slight bump-outward shape of the wires can be used to appropriately expand the wires away from the axis when pushed.

In some embodiments, the size determining portion 202 can have two, three, four, five or more wires 210, and the number of wires 210 is not limiting. In some embodiments, the wires 210 can be made of metal (e.g., nitinol) or polymer, though the type of material is not limiting.

In some embodiments, the wires 210 can be formed as round wires, though the shape of the wires is not limiting. In some embodiments, the wires 210 cart be cut from a plastic or a metal tube. In some embodiments, the entire device 200 can be formed from laser cut nitinol tubing. In some embodiments, the wires 210 can form a helix. In some embodiments. the wires 210 can form counter-wound helixes. In some embodiments, the wires 210 can form a braid. In some embodiments, the wires 210 can be covered with a flexible membrane. 'The flexible membrane can be biocompatible and can prevent any problems using non- biocompatible wires 210. In some embodiments, the flexible membrane may be an elastic material, though the type of material is not limiting.

The wires 210 can be connected to a blocking mechanism 204. The distal ends of the wires 210 may connect to the blocking mechanism 204 at a substantially perpendicular angle, as shown in FIGS. 2A-R However, the general angle of connection is not limiting, and other angles can be used. In some embodiments, the blocking mechanism 204 can be secured to the wall of the deployment catheter 206, thus preventing motion of the blocking mechanism 204 relative to the catheter. Accordingly, when a user pushes the wires 210 against the blocking mechanism 204 seemed to the wall of the deployment catheter 206, the wires 210 can expand outward and away from each other while the catheter 206 and blocking mechanism 204 remain in the same position.

FIG. 2B illustrates: the blocking mechanism 204 and wires 210 being located within the catheter 206, which can further be located within the lumen 212 of an airway. As shown, the catheter 206 and device 200 can have a generally circular cross-section, though the particular cross section is not limiting. Further, as shown the wires 210 can extend away from the center of the lumen 212 and towards the inner surface of the lumen 212.

The size determining portion 202 can be deployed inside the lumen 212 for measurement of the lumen 212. In some embodiments, a shaft (not shown) can be used to adjust the position of the sizing device 200, and thus the size determining portion 202, within an airway lumen. For example, a shaft similar to the ones described above can be used to move the size determining portion 202. In some embodiments, the shaft can be attached to the sizing device 200. In some embodiments, the shaft can be integrally formed with the sizing device 200.

In some embodiments. the wires 210 can be secured to the wall of the deployment catheter and limit the longitudinal movement of the sizing device 200, without the blocking mechanism 204. The distance the wire 210 can be pushed before contact with the lumen 212 can correlate to the lumen size and provide a user with the size of the lumen that the sizing device 200 is deployed in. A user may detect the lumen size by reading the distance the wires 210 are pushed (e.g., via a linear measurement at a proximal end of the wires) until the wires touch the lumen wall.

In some embodiments, the size determining portion 202 and blocking mechanism 204 can be inserted into a deployment catheter and/or sheath 206 for deployment of in the lumen 212 of an airway. Accordingly, the catheter 206 can be positioned to allow for the sizing device 200 to determine the size of a particular portion of an airway lumen. In some embodiments, the wires 210 can exit from the side of the deployment catheter 206 through, for example, cutouts, as shown in FIG. 2A.

In some embodiments, a similar configuration to that shown in FIGS. 2A-B can be used, except the wires 210 can expand radially outward when the blocking mechanism 204 is pulled proximally instead of the wires 210 being pushed distally. Accordingly, the motion is generally opposite of what is discussed above, though the structure is generally similar.

In some embodiments, the proximal portions of the wire 210 can be secured to inhibit or prevent any longitudinal movement relative to the lumen wall 212. Similar to the above configuration, the distance the wire 210 can be compressed (or the amount the blocking mechanism 204 can be pulled) can be related to the lumen size. A user may detect the lumen size by reading the distance the wires 210 are compressed until the wires 210 touch the lumen wall 212.

Caliper-Type Sizing Device

Figure 3A:
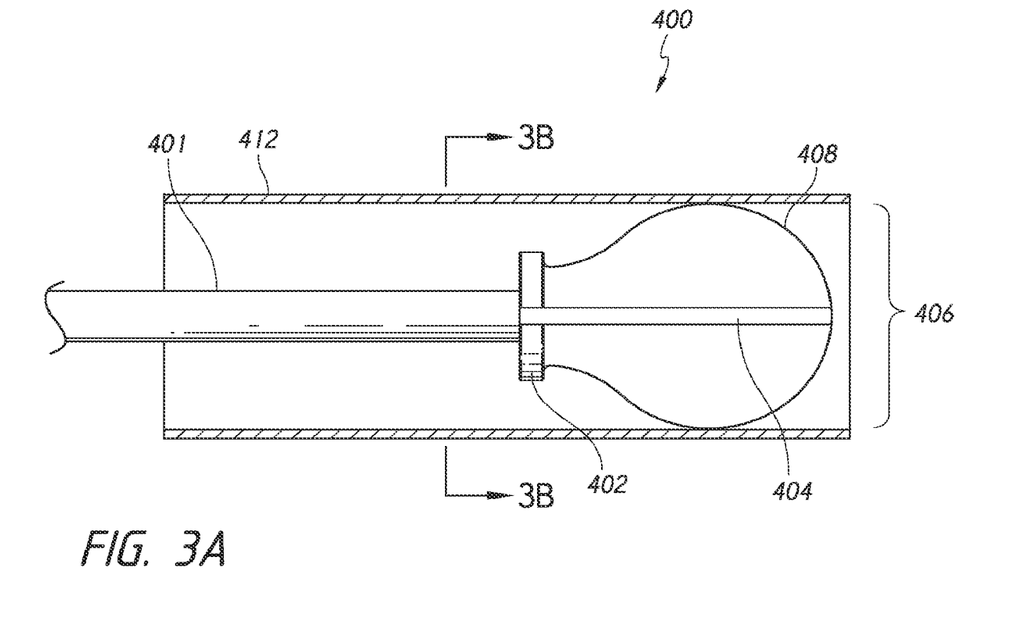
FIGS. 3A-B illustrate viewpoints of an embodiment of a caliper-type airway measuring device.
Figure 3B:
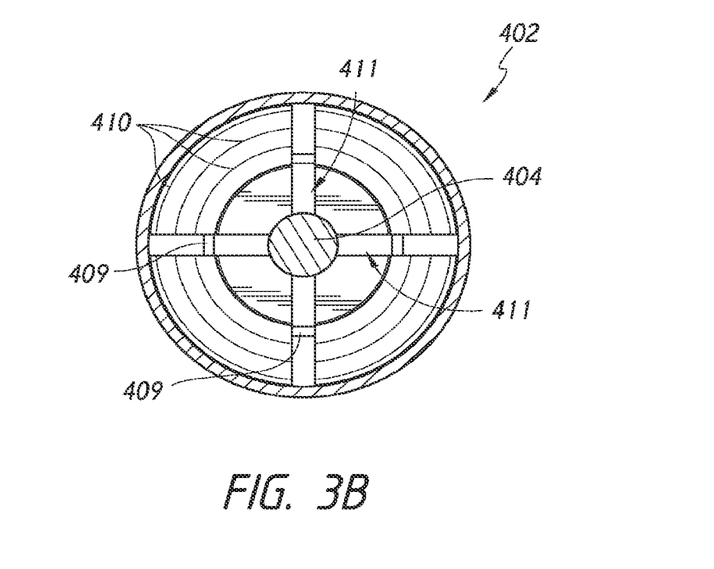

FIGS. 3A-B show another embodiment of a sizing device for determining or estimating the size of airway lumens. As shown, an endoluminal sizing device 400 can be made up of a measuring disc 402, a centering portion 404, and a size determining portion 406. Similar to the devices listed above, the size determining portion 406 can deploy (e.g., expand) inside the lumen of an airway 412, for example upon release from a sheath. In some embodiments, the sizing device 400 can be located on the end of a shaft or catheter 401, as shown in FIG. 3A. This can allow a user to move the sizing device 400 to a particular location in an airway in order to measure it. Other methods of insertion can be used, and the method of insertion and translation of the sizing device 400 is not limiting.

Attached to the end of the shaft 401 can be the measuring disc 402 which can be used to measure the expansion of the size determining portion 406, though in some embodiments the measuring disc 402 can at least partially encircle the shaft 401. The measuring disc 402 can be generally circular in shape as shown in FIG. 3B, though the particular shape is not limiting. In some embodiments, the measuring disc 402 can be generally transparent or translucent to allow for a user to see through the measuring disc 402 to the size determining portion 406 beyond. In some embodiments, the measuring disc 402 is opaque. In some embodiments, the measuring disc 402 can be centered onto the shaft 401. In some embodiments, the measuring disc 402 can be integrally formed onto the shaft 401. In some embodiments, the measuring disc 402 can be attached to the shaft 401 through different means, such as mechanical, chemical, and adhesive.

In some embodiments, as shown in FIG. 3B the measuring disc 402 can have different marking 410 to reflect sizes. 'The markings 410 can be seen by a user in order to determine the size of an airway lumen. For example, the measuring disc 402 can have different rings showing different sizes, as shown as the circular markings 410 in FIG. 3B. Different types of markings 410 can be used as well, and the type of markings 410 is not limiting. Further, different combinations of markings 410 can be used, or a single type of marking 410 can be used.

A centering portion 404 can be connected to the measuring disc 402 opposite the shaft 401. In some embodiments, the centering portion 404 can be a wire or a tube. In some embodiments, the centering portion 404 can be generally rigid. In some embodiments, the centering portion 404 can be generally flexible. The centering portion 404 can be used to connect and align the measuring disc 402 and the size determining portion 406 along the axis of the lumen 412.

In some embodiments, the size determining portion 406 can be composed of one or more struts 408 that can contract or expand according to the sizing of the lumen wall 412. The struts 408 can be, for example, wires, though the particular makeup of the struts 408 is not limiting. In some embodiments, the struts 408 can form an expandable basket or a balloon shaped portion.

In some embodiments, the struts 408 can be a combination of two or more of the aforementioned shapes, such as a plurality of wires and a balloon/basket shape, and the particular combination is not limiting. In some embodiments, the struts 408 can be formed from nitinol, though the material is not limiting.

As mentioned, the centering portion 404 can be flexible, and can thus allow some motion of the centering portion 404 and the connected struts 408. If the centering portion 404 is flexible enough, it will allow the struts 408 to center the size determining portion 406 within a lumen 412. The flexible centering portion 404 thus allows for the struts 408 to all compress in relatively the same manner, thereby centering the size determining portion 406, and none of the struts 408 may be under or overcompressed as compared to the other struts 408.

In some embodiments, the size determining portion 406 can contract when placed inside the lumen. The degree of contraction can be scaled based on the measuring disc marking 410. Once the size determining portion 406 is placed inside the lumen wall a user can view from the endoscope the size of the lumen by reading the location of the struts 408 with respect to the measuring disc marking 410.

In some embodiments, the struts 408 have generally free ends 409, such as the proximal ends, that extend within channels, or tracts, 411 in the measuring disc 402 and can move freely. Therefore, as the struts 408 expand outwards to contact the lumen 412, the free ends 409 can move within the channels 411 of the measuring disc 402. Thus. a user can view the measuring disc 401 and visualize where the free ends 409 are located, and can calculate the dimensions of the lumen 412. The measuring disc 402 can also contain a plurality of markings 410 that can be viewed by a user, and the user can compare the markings 410 to the free ends 409 to determine the size of the lumen 412. In some embodiments, the free ends 409 can be marked or can fluoresce in order to be easier for a user to visualize.

In some embodiments, the proximal end of the size determining portion 406 can connect to the measuring disc 402 without a separate connecting mechanism. In some embodiments, the measuring disc 402 and the size determining portion 406 are connected by a connecting mechanism, such as the centering portion 404 shown in FIG. 3A. In some embodiments, the connecting mechanism may include a centering mechanism to center the connecting mechanism substantially near the axis of the lumen.

Circumscribing-Type Sizing: Device

Figure 4:
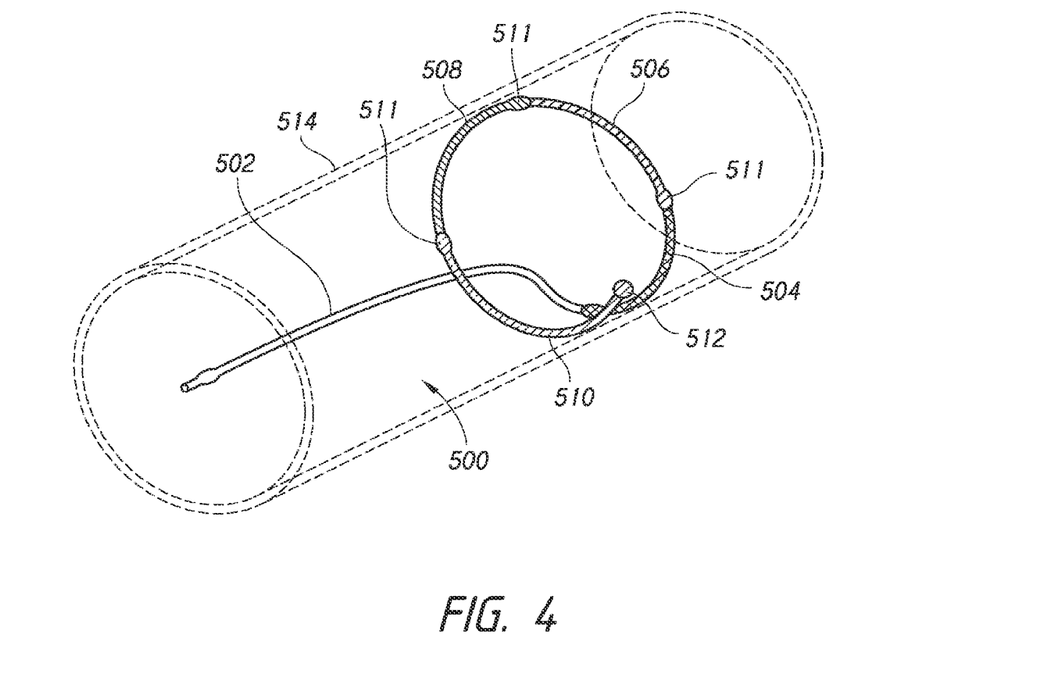
FIG. 4 illustrates a viewpoint of an embodiment of a circumscribing-type airway measuring device.

FIG. 4 illustrates another embodiment of a sizing device 500. In some embodiments, the device 500 can have a shaft 502 that extends in a lumen 514. The shaft 502 can be, for example, wires, metals, or polymers, and the type of material is not limiting. The shaft 502 can curve radially outwards, as shown in FIG. 4. Thus, a generally spiral shape can be formed in the lumen 514 and can generally wrap around (circumscribe) the lumen.

The device 500 can include a plurality of different portions 504/506/508 which can be visually different to indicate different sizing to a user. For example, the different portions 504/506/508 can be different colors, markings, or protrusions for ease of viewing. The portions 504/506/508 can be separated by different protrusions 511. At the end, the device 500 can have a measuring portion 510 having a free end 512.

Thus, when in use, the portions 504/506/508 can extend and contact in the lumen 514, depending on the size of the lumen 514. From viewing the free end 512, a user can determine the size of the lumen. For example, a smaller lumen would contract the radius of portions 504/506/508, and thus the free end 512 would be located at a different position on the portions 504/506/508 than if the lumen was larger. The position of the free end 512 can be viewed by a user to determine the size of the lumen 514. Accordingly, the amount of overlap can indicate (by markings) the circumference of the lumen 514 in the plane of contact.

In some embodiments, the free end 512 may be attached to the portions 504/506/508 in order to slide along the portions 504/506/508. In some embodiments, the free end 512 is proximal to the portions 504/506/508. In some embodiments, the free end 512 is distal to the portions 504/506/508.

From the foregoing description, it will be appreciated that an inventive airway lumen sizing device is disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations and/or "some embodiments" can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations Also, the separation of various system components m the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount. or characteristic close to the stated value, amount, or characteristic that still performs a desired function or achieves a desired result For example, the terms "approximately", "about', "generally,", md 'substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents 'without departing from the unique and inventive disclosure herein or the scope of the claims.

What is claimed is:

1. An endoluminal sizing device comprising:
    a deployment sheath including a lumen;
    a shaft movable along an axis of the lumen;
    a blocking mechanism including a cylindrical body filling a distal end of the lumen of the deployment sheath and affixed to an inner surface of the lumen; and
    a size determining portion attached to the shaft, the size determining portion comprising a plurality of expandable members affixed to a proximal end of the blocking mechanism, wherein the plurality of expandable members are configured to expand through apertures in the deployment sheath to an endoluminal wall of the lumen upon distal movement of the shaft;
    wherein the size determining portion comprises an indication of a size of a body lumen.

2. The endoluminal sizing device of claim 1, wherein the deployment sheath at least partially surrounds the size determining portion, wherein the deployment sheath includes a plurality of cutouts that allow for expansion of the plurality of expandable members radially outward to the endoluminal wall.

3. The endoluminal sizing device of claim 1, wherein a distal surface of the blocking mechanism forms a distal end of the size determining portion, the plurality of expandable members comprise a plurality of wires extending perpendicular from the proximal end of the blocking mechanism;
  wherein compressing the plurality of wires against the blocking mechanism radially expands the plurality of wires to contact the endoluminal wall;
  wherein a change in a longitudinal distance of the plurality of wires before and after the size determining portion contacts the endoluminal wall indicates the sizing of the body lumen.

4. The endoluminal sizing device of claim 3, wherein compressing occurs by a force acting on the plurality of wires.

5. The endoluminal sizing device of claim 3, wherein compressing occurs by a force acting on the blocking mechanism.

6. A method of using an endoluminal sizing device for sizing a body lumen comprising:
  deploying the endoluminal sizing device inside the body lumen, the endoluminal sizing device comprising:
  a deployment catheter including a lumen;
  a blocking mechanism including a cylindrical body blocking a distal end of the lumen of the deployment catheter and affixed to an inner surface of the lumen;
  a shaft movable along an axis of the lumen of the deployment catheter;
  a size determining portion, the size determining portion comprising a plurality of expandable members extending between the shaft and the blocking mechanism,
  wherein the plurality of expandable members are configured to expand to an endoluminal wall of the body lumen through apertures in the deployment catheter; and
  determining an endoluminal size from a distance of movement of the shaft.

7. The method of claim 6, wherein the plurality of expandable members comprising a plurality of wires extending substantially perpendicular from a proximal face of the blocking mechanism when in a relaxed state,
  wherein compressing the plurality of wires against the blocking mechanism radially expands the plurality of wires to contact the endoluminal wall; and
  wherein a change in a longitudinal distance of the plurality of wires before and after the size determining portion contacts the endoluminal wall indicates the sizing of the body lumen.

8. The method of claim 7, wherein compressing occurs by a force acting on the plurality of wires.

9. The method of claim 7, wherein compressing occurs by a force acting on the blocking mechanism.

10. An endoluminal sizing device comprising:
  a deployment catheter;
  a blocking mechanism including a cylindrical body blocking a distal end of a lumen of the deployment catheter and secured to an inner surface of the lumen; and
  a size determining portion including a plurality of wires coupled to a shaft, the plurality of wires extending proximally within a portion of the deployment catheter from a proximal face of the blocking mechanism, each wire of the plurality of wires configured to bend in a pre-determined direction upon compression of the size determining portion.

11. The endoluminal sizing device of claim 10, wherein compression of the size determining portion occurs in response to movement of the shaft distally within the deployment catheter.

12. The endoluminal sizing device of claim 11, wherein the shaft includes lumen measurement indications.

13. The endoluminal sizing device of claim 10, wherein the deployment catheter includes cutouts positioned to receive portions of the plurality of wires.

14. The endoluminal sizing device of claim 10, wherein each wire of the plurality of wires includes a shapeset outward bend.

15. The endoluminal sizing device of claim 10, wherein the plurality of wires form a helix within the deployment catheter.

* * * * *